United States Patent

Varaprath et al.

[11] Patent Number: 5,270,036
[45] Date of Patent: Dec. 14, 1993

[54] PERMANENT WAVING WITH SILICONES

[75] Inventors: Padmakamuri J. Varaprath; Judith M. Vincent, both of Midland, Mich.

[73] Assignee: Dow Corning Corporation, Midland, Mich.

[21] Appl. No.: 959,892

[22] Filed: Oct. 13, 1992

[51] Int. Cl.$^5$ ............ H61K 7/09; H61K 33/40
[52] U.S. Cl. ............................ 424/71; 424/616; 132/204
[58] Field of Search ............ 424/71, 70, 47, 616; 132/204

[56] References Cited

U.S. PATENT DOCUMENTS

| | | | |
|---|---|---|---|
| 3,987,127 | 10/1976 | Dickie | 522/107 |
| 4,401,500 | 8/1983 | Hamada | 524/588 |
| 4,585,669 | 4/1986 | Eckberg | 528/24 |
| 4,654,382 | 3/1987 | Hiza | 525/502 |
| 4,770,873 | 9/1988 | Wolfram | 424/71 |
| 4,798,722 | 1/1989 | Edman | 424/71 |
| 4,849,564 | 7/1989 | Shimuzu | 524/114 |
| 4,987,180 | 1/1991 | Ohata | 524/862 |
| 5,045,310 | 9/1991 | Halloran | 424/71 |
| 5,171,638 | 12/1992 | Ozaki | 524/837 |

*Primary Examiner*—Paul R. Michl
*Assistant Examiner*—Sally Gardner
*Attorney, Agent, or Firm*—James L. DeCesare

[57] ABSTRACT

A process for permanent waving of hair by a reaction in which cystine bridges are reduced to cysteine, the hair reshaped, and the reaction reversed. The improvement in the process resides in the step of reversing the reaction by applying to hair a composition which includes a vinyl functional silicone, a carrier fluid, and an oxidizing agent such as hydrogen peroxide. Permanent hair waving neutralizer compositions are also described.

3 Claims, No Drawings

5,270,036

PERMANENT WAVING WITH SILICONES

BACKGROUND OF THE INVENTION

This invention is directed to a method of waving hair and to a silicone based neutralizer composition useful in the permanent waving of hair.

Keratin is a fibrous protein composed of eighteen different kinds of amino acids. It is widely distributed in hair and constitutes the major component thereof. Keratin is characterized by a crosslinked structure having one disulfide bond —S—S— per average 10–20 amino acid residues. It is most frequently represented as cystine which has the formula $HO_2CC(NH_2)HCH_2S-SCH_2C(NH_2)HCO_2H$.

The first basic step in a permanent waving process is the partial reduction of cystine $HO_2CC(NH_2)HCH_2S-SCH_2C(NH_2)HCO_2H$ to cysteine $HO_2CC(NH_2)HCH_2SH$. Typically, a waving lotion containing thioglycolic acid is used in this step in a reaction in which cystine bridges are reduced to cysteine. After the hair has been reshaped, this reaction is reversed by the application to the hair of a neutralizer which is a solution containing an oxidant such as hydrogen peroxide. Cysteine residues formed during the reduction step are converted back into cystine upon neutralization.

There exists a need in the art for alternative forms of permanent waving neutralizer compositions. The present invention provides such an alternative in the form of a silicone based composition which has been found to effectively function as a keratin crosslinking agent in conjunction with an oxidizing agent such as hydrogen peroxide, in the permanent waving of human hair. It is believed that the silicone becomes part of a covalent crosslink between hair keratin fibers in providing a wave. In addition, use of the silicone has the advantage that the silicone imparts to the hair added benefits such as conditioning of the hair to provide hair that feels smoother and silkier, and which has improved combing properties.

SUMMARY OF THE INVENTION

The invention relates to a hair waving process and to a composition for use in the process. More particularly, a silicone based neutralizer is employed to reform cystine-like structures from cysteine residues produced during the reduction phase of the permanent waving process. The neutralizer composition of the present invention includes a vinyl functional silicone, an oxidizing agent such as hydrogen peroxide, and a carrier fluid.

When used in conjunction with hydrogen peroxide based neutralizer solutions, the composition of the present invention possesses the advantage of simultaneously functioning as a keratin crosslinking agent, while at the same time imparting to the hair conditioning benefits.

These and other objects, features, and advantages, of the present invention should become more apparent from a consideration of the following detailed description thereof.

DETAILED DESCRIPTION OF THE INVENTION

The neutralizer composition includes as essential ingredients a vinyl functional silicone, an oxidizing agent such as hydrogen peroxide, and a suitable carrier fluid for delivering the active ingredients. The composition may additionally contain wetting and foaming agents to improve spreading and retention of the composition on the hair, as well as other conditioning agents to enhance a smooth texture, improve ease of combing, and to increase control of fly-away.

Both cyclic and linear vinyl functional silicones may be used. Suitable vinyl functional silicones comprehended as being within the scope of the invention are compounds which can be represented by the following formulas:

(I)

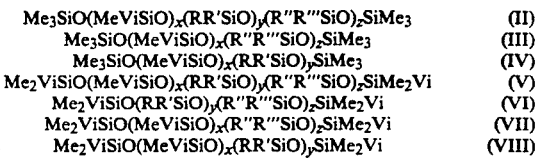

| | |
|---|---|
| $Me_3SiO(MeViSiO)_x(RR'SiO)_y(R''R'''SiO)_zSiMe_3$ | (II) |
| $Me_3SiO(MeViSiO)_x(R''R'''SiO)_zSiMe_3$ | (III) |
| $Me_3SiO(MeViSiO)_x(RR'SiO)_ySiMe_3$ | (IV) |
| $Me_2ViSiO(MeViSiO)_x(RR'SiO)_y(R''R'''SiO)_zSiMe_2Vi$ | (V) |
| $Me_2ViSiO(RR'SiO)_y(R''R'''SiO)_zSiMe_2Vi$ | (VI) |
| $Me_2ViSiO(MeViSiO)_x(R''R'''SiO)_zSiMe_2Vi$ | (VII) |
| $Me_2ViSiO(MeViSiO)_x(RR'SiO)_ySiMe_2Vi$ | (VIII) |

In the above formulas, n is an integer having a value of three to about thirty. Preferably n is five. R, R', R", and R''', each represent an alkyl group of one to six carbon atoms or phenyl. Preferably R, R', R", and R''' are each methyl. Me is methyl. Vi is $CH_2=CH-$. The integers x, y, and z, each have a value of one to about one thousand. Formula (I) represents a cyclic vinyl functional silicone, while the remainder of the Formulas (II) to (VIII) are representations of linear materials. Such vinyl functional silicones as compounds are known in the art, as are methods for their preparation. The compounds are all commercially available.

While the silicone compounds shown above in Formulas I–VIII are operative in accordance with the concepts of the present invention, vinyl functional silicones particularly preferred herein are compounds possessing a low degree of polymerization and a high content of the vinyl functionality. Representative vinyl functional silicones are shown below, in which the groups Me and Vi, and the integer x, have the same meaning and value as previously described:

| | |
|---|---|
| $Me_2ViSiO(MeViSiO)_xSiMe_2Vi$ | (IX) |
| $Me_2ViSiOSiMe_2Vi$ | (X) |

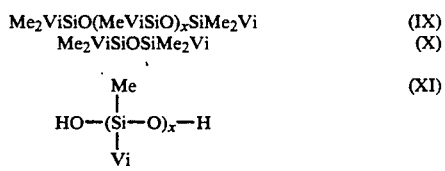

(XI)

The value of the integer "x" in Formulas IX and XI is from one to one thousand. In Formula IX, x preferably has a value of from one to fifty. In Formula XI, x preferably has a value of ten to one thousand, and most preferably a value of ten to one hundred.

The compound identified by Formula X is divinyltetramethyldisiloxane, and this vinyl functional disiloxane may further be used in the form of a mechanical emulsion containing about thirty-five percent by weight of the disiloxane. In the examples and tables which follow, the disiloxane of Formula X is identified as "Silicone 1", while the mechanical emulsion of the disiloxane is identified as "Silicone 2". Formula XI represents an emulsion polymer prepared by emulsion polymerizing cyclic methylvinylsiloxanes. In the examples and tables which follow, this emulsion polymer is identified as "Silicone 3". Formula IX represents another emulsion polymer prepared by emulsion polymerizing divinyltetramethyldisiloxane and a cyclic methylvinylsiloxane. In the examples and tables which follow, this emulsion polymer is identified as "Silicone 4". The particular polymer used as "Silicone 4" had a degree of polymerization of about ten.

Techniques for the preparation of mechanical emulsions, and techniques for making emulsions using emulsion polymerization, are well known in the art, and any standard technique may be used to prepare the mechanical emulsions, and the emulsion polymers, described above. The interested reader is referred to European Patent Application 0460683A2 published Dec. 11, 1991, for a technique for the preparation of mechanical emulsions, and European Patent Application 0459500A2 published Dec. 4, 1991, for a technique for the preparation of emulsion polymers.

Mechanical emulsions are prepared by mixing the silicone in water with one or more surfactants. Anionic, nonionic, and cationic, surfactants can be employed to help stabilize the emulsion. For improved stability, it is often advantageous to use a mixture of two or more surfactants, such as combinations of two nonionic surfactants, an anionic and a nonionic surfactant, or a cationic and nonionic surfactant. Typically, from one to thirty parts by weight of surfactant are used per one hundred parts by weight of the silicone.

In emulsion polymerization, there is combined a reactive silicone oligomer, a surfactant, a polymerization catalyst, and water. The mixture is stirred and the silicone oligomers are allowed to polymerize until an emulsion is formed. Typically, alkoxysilanes or cyclic siloxanes are used as the reactive monomers and oligomers. Combinations of silicone reactants can be employed to form copolymers in the resulting emulsion.

The concept of the crosslinking of human hair with a vinyl functional silicone is believed to take place in accordance with the mechanism shown below, in which a cyclic vinyl functional silicone is used for purposes of illustration.

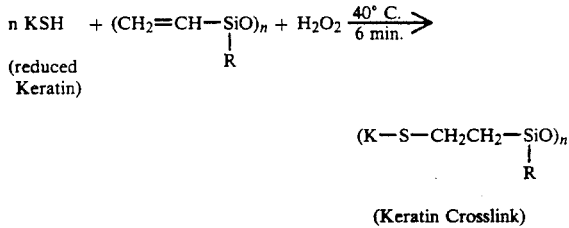

In the above scenario, K is $HO_2CC(NH_2)HCH_2-$, or a polymeric derivative thereof.

As a carrier fluid, there may be used alcohols, hydrocarbons, halogenated hydrocarbons, water, mixtures of alcohol and water, or volatile silicones. Representative carrier fluids which may be mentioned are ethanol, isopropyl alcohol, mineral spirits, trichloroethane, and dichlorotetrafluoroethane.

Where it is desired to use a silicone carrier fluid, the volatile silicone in accordance with the present invention is a low viscosity methylsilicone fluid. The volatile low viscosity methylsilicone fluid corresponds to the average unit formula $(CH_3)_aSiO_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methylsilicone fluid, whereby the methylsilicone fluid has a viscosity of less than about one hundred centistokes measured at twenty-five degrees Centigrade.

The volatile low viscosity methylsilicone fluid contains dimethylsiloxane units and optionally trimethylsiloxane units. Preferably, the methylsilicone fluid has a viscosity of less than about ten centistokes. Representative compounds are cyclopolysiloxane compounds of the general formula $[(CH_3)_2SiO]_x$, and linear siloxane compounds of the general formula $(CH_3)_3SiO[(CH_3)_2SiO]_ySi(CH_3)_3$, in which x is an integer having a Value of from three to ten, and y is an integer having a value of from zero to about four.

The volatile low viscosity methylsilicones have boiling points generally less than about two hundred-fifty degrees Centigrade, and possess viscosities preferably generally less than about ten centistokes measured at twenty-five degrees Centigrade. Most preferably, the viscosity is 0.65 to 5.0 centistokes. The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative methylsilicone fluids found to be especially useful in accordance with the present invention are hexamethyldisiloxane which has a boiling point of 99.5 degrees Centigrade and the formula $Me_3SiOSiMe_3$; octamethyltrisiloxane which has a boiling point of 152 degrees Centigrade and the formula $Me_3SiOMe_2SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $(Me_2)SiO]_4$; and decamethylcyclopentasiloxane which has a boiling point of 205 degrees Centigrade and the formula $[(Me_2)SiO]_5$.

These methylsilicone fluids may be used alone, or as mixtures in combinations of two or more. Mixtures of the methylsilicone fluids will result in a volatile material having an evaporating behavior different from any one of the individual methylsilicone fluids. The methylsilicone fluids and methods for their preparation are known in the art, and such fluids are commercially available.

In some instances, it may be desirable to replace one or more of the methyl groups in the methylsilicone fluid with other groups. Thus, there may be substituted groups such as alkyl radicals having two to twelve carbon atoms; aryl radicals having six to ten carbon atoms; amine groups; vinyl; hydroxyl; haloalkyl groups; aralkyl groups: and acrylate groups, for example.

The composition of the present invention is suitable for use in permanent waving processes which may be characterized as hot wave processes, mild wave processes, and cold wave processes. In a typical cold wave process for example, the hair is first shampooed, and the freshly shampooed and still damp hair is divided into about forty to sixty tresses. Each tress is wetted with the waving lotion and wound onto plastic curlers. The size of the curler determines the nature of the resultant wave. Small curlers for example result in tighter waves. The hair is rinsed thoroughly, and neutralized with the neutralizer solution. The hair is then unwound, rinsed again, and either dried or set into a desired style.

The composition according to the present invention contains from 0.1 to 10.0 percent by weight of a vinyl functional silicone, 0.1 to 5.0 percent by weight of an oxidizing agent such as hydrogen peroxide, and 85.0 to 99.8 percent by weight of a carrier fluid. The following examples are set forth for the purpose of illustrating the invention in more detail.

EXAMPLE I

Hair tresses were prepared by gluing 2.4 grams of eight inch long dark brown virgin European hair to a two inch square plastic tab. After allowing the glue to cure, each tress was trimmed to a length of six inches. The tresses were shampooed by rinsing the tresses with forty degree Centigrade tap water, applying 0.5 milliliters of a shampoo based on sodium lauryl sulfate for thirty seconds, and rinsing the tresses for thirty seconds.

EXAMPLE II

The hair tresses were clamped to a bench and the hair was combed. One gram of permanent waving reducing solution was applied to each tress and combed through the hair. Using standard permanent waving end paper, the hair was wrapped on a permanent waving rod, and one gram of additional permanent waving reducing solution was applied to the hair with a syringe. The rolled hair was allowed to set for fifteen minutes. In order to simulate the conditions of the human head, the rolled-up hair tresses were transferred to a plastic bag and the bag was placed in an oven at forty degrees Centigrade for ten minutes.

EXAMPLE III

The rolled hair tresses were removed from the oven and rinsed under warm tap water for one minute. The tresses were blotted dry with a paper towel. Each tress was placed in a weighing dish and 1.5 grams of neutralizer solution was applied with a syringe. An additional two grams of the neutralizer was added to the weighing dish. After five minutes, the tresses were unwrapped from the rod, and excess neutralizer was worked out of the tresses and back into the weighing dish. The hair tresses were rinsed under tap water for one minute and hung to dry at room temperature.

EXAMPLE IV

After the elapse of two days, the tresses were prepared for evaluation. This procedure involved labelling both sides of each tress "left" and "right", and the tress was cut in half lengthwise. The "right" half was shampooed by rinsing in forty degree Centigrade tap water, applying 0.25 milliliters of blank shampoo, and rinsing the tress for fifteen seconds. The shampoo treatment was repeated four times on the "right" half tresses, and allowed to dry. The "right" half tresses were evaluated against the unwashed "left" half tresses.

Evaluations were conducted using the foregoing procedures of Examples I–IV. As "controls", there was employed two commercially available permanent waving kits, one including a reducing solution containing thioglycolic acid, and the other including a reducing solution containing glyceryl monothioglycolate. The neutralizer solution available with each of these commercial products was employed in the oxidizing step. As an alternate "control", a solution containing 7.6 percent by weight of thioglycolic acid in water was used, and the pH of this alternate control was adjusted to 9.5 with ammonium hydroxide. The alternate "control" is referred to in the Tables which follow as the "THIO BLANK". The "THIO BLANK" was neutralized with a two percent solution of hydrogen peroxide in water, with the pH being adjusted to between 3.4–3.7 with phosphoric acid.

The composition of the present invention was evaluated against these controls in three different ways. In "Method A", two percent of a vinyl functional silicone was added to the permanent waving reducing solution. In "Method B", two percent of a vinyl functional silicone in water or in a mixture of water and alcohol, was applied as an intermediate step between the reduction and neutralization steps. In "Method C", two percent of a vinyl functional silicone was added to the neutralizer solution.

The evaluations were conducted after the permed hair tresses had been prepared in accordance with Examples I–IV, and after the prepared tresses had been cut lengthwise and the "right" half shampooed as in Example IV. Both the unwashed "left" half and the washed "right" half were evaluated using subjective sensory criteria for establishing ratings on the amount of curl, ease of combing, and softness of feel. A rating scale of one to five was used, with one indicating the best and five indicating the worst. The evaluations were performed by the technician carrying out the procedure. Incremental differences in units of 0.25 were tabulated. The results of these evaluations are set forth in Tables I and II.

Table I establishes improvements over the controls in all categories of sensory testing. The best results were obtained with the "THIO BLANK". In Table II, there is shown a comparison between the controls and the compositions of the invention, in terms of deterioration in curl, combing, and feel, following five shampoos. Significantly less deterioration is evident especially with the "THIO BLANK".

TABLE I

| Permanent | Silicone | Method | Curl Unwash | Wash | Combing Unwash | Wash | Feel Unwash | Wash |
|---|---|---|---|---|---|---|---|---|
| Commercial | — | — | 2.5 | 3.38 | 3.25 | 3.5 | 2.66 | 3.25 |

TABLE I-continued

| Permanent | Silicone | Method | Curl Unwash | Curl Wash | Combing Unwash | Combing Wash | Feel Unwash | Feel Wash |
|---|---|---|---|---|---|---|---|---|
| Control for Silicone 1 | | | | | | | | |
| Commercial | 1 | B | 2.66 | 3.75 | 3.0 | 3.5 | 3.0 | 2.66 |
| Commercial | — | — | 2.5 | 2.62 | 2.38 | 2.5 | 3.5 | 3.88 |
| Control for Silicone 2 | | | | | | | | |
| Commercial | 2 | A | 2.12 | 2.25 | 2.0 | 2.81 | 3.25 | 3.38 |
| Commercial | 2 | B | 2.12 | 2.38 | 2.38 | 2.75 | 3.12 | 3.12 |
| Commercial | 2 | C | 2.25 | 2.62 | 2.50 | 2.88 | 3.12 | 3.5 |
| Commercial | — | — | 2.5 | 2.75 | 2.38 | 2.5 | 3.5 | 3.88 |
| Control for Silicones 3 & 4 | | | | | | | | |
| Commercial | 3 | A | 2.38 | 2.62 | 2.0 | 2.44 | 3.0 | 3.25 |
| Commercial | 3 | B | 2.12 | 2.12 | 1.94 | 2.19 | 2.88 | 3.25 |
| Commercial | 3 | C | 2.0 | 2.12 | 2.0 | 2.44 | 3.0 | 3.25 |
| Commercial | 4 | A | 2.0 | 2.12 | 2.0 | 2.44 | 2.88 | 3.12 |
| Commercial | 4 | B | 2.12 | 2.25 | 1.94 | 2.0 | 2.88 | 3.25 |
| Commercial | 4 | C | 2.25 | 2.38 | 2.31 | 2.44 | 3.0 | 3.12 |
| Thio Blank | — | — | 3.12 | 3.5 | 3.0 | 3.5 | 3.12 | 3.75 |
| Control for Silicone 1 | | | | | | | | |
| THIO BLANK | 1 | A | 3.25 | 2.75 | 3.25 | 3.75 | 3.0 | 3.5 |
| THIO BLANK | 1 | B | 3.75 | 3.62 | 2.25 | 3.12 | 2.66 | 3.12 |
| Thio Blank | — | — | 2.12 | 2.62 | 2.19 | 2.88 | 2.62 | 3.5 |
| Control for Silicone 2 | | | | | | | | |
| THIO BLANK | 2 | B | 2.38 | 2.38 | 2.44 | 2.56 | 2.62 | 3.0 |
| THIO BLANK | 2 | C | 2.38 | 2.38 | 2.25 | 2.56 | 2.62 | 3.12 |
| Thio Blank | — | — | 2.12 | 2.62 | 2.19 | 2.88 | 2.62 | 3.5 |
| Control for Silicones 3 & 4 | | | | | | | | |
| THIO BLANK | 3 | B | 1.5 | 1.75 | 1.56 | 2.19 | 2.0 | 2.62 |
| THIO BLANK | 3 | C | 1.88 | 1.75 | 1.88 | 2.19 | 2.0 | 2.5 |
| THIO BLANK | 4 | B | 2.38 | 2.5 | 2.16 | 2.32 | 2.25 | 2.88 |
| THIO BLANK | 4 | C | 2.5 | 2.0 | 2.31 | 2.25 | 2.75 | 2.75 |

TABLE II

| Permanent | Silicone | Method | Curl | Combing | Feel |
|---|---|---|---|---|---|
| Commercial | — | — | −0.88 | −0.25 | −0.59 |
| Control for Silicone 1 | | | | | |
| Commercial | 1 | B | −0.59 | −0.50 | +0.34 |
| Commercial | — | — | −0.12 | −0.12 | −0.38 |
| Control for Silicone 2 | | | | | |
| Commercial | 2 | A | −0.13 | −0.43 | −0.13 |
| Commercial | 2 | B | −0.26 | −0.37 | 0 |
| Commercial | 2 | C | −0.37 | −0.38 | −0.38 |
| Commercial | — | — | −0.25 | −0.12 | −0.38 |
| Control for Silicones 3 & 4 | | | | | |
| Commercial | 3 | A | −0.24 | −0.44 | −0.25 |
| Commercial | 3 | B | 0 | −0.25 | −0.38 |
| Commercial | 3 | C | −0.12 | −0.44 | −0.50 |
| Commercial | 4 | A | −0.12 | −0.44 | −0.24 |
| Commercial | 4 | B | −0.12 | −0.06 | −0.38 |
| Commercial | 4 | C | −0.12 | −0.13 | −0.12 |
| Thio Blank | — | — | −0.38 | −0.5 | −0.63 |
| Control for Silicone 1 | | | | | |
| THIO BLANK | 1 | A | +0.50 | −0.5 | −0.5 |
| THIO BLANK | 1 | B | +0.13 | −0.88 | −0.50 |
| Thio Blank | — | — | −0.50 | −0.69 | −0.88 |
| Control for Silicone 2 | | | | | |
| THIO BLANK | 2 | B | 0 | −0.12 | −0.38 |
| THIO BLANK | 2 | C | 0 | −0.41 | −0.50 |
| Thio Blank | — | — | −0.50 | −0.68 | −0.93 |
| Control for Silicones 3 & 4 | | | | | |
| THIO BLANK | 3 | B | −0.25 | −0.63 | −0.62 |
| THIO BLANK | 3 | C | +0.13 | −0.31 | −0.50 |
| THIO BLANK | 4 | B | −0.12 | −0.16 | −0.63 |
| THIO BLANK | 4 | C | +0.50 | +0.06 | 0 |

The compositions of the present invention may contain other ingredients in addition to the vinyl functional silicone, the oxidizing agent, and the carrier fluid. For example adjuvants common to permanent waving and neutralizing compositions may be employed as adjuvants. For example, adjuvants which may be included are reducing agents, coloring agents, perfume oils, opacifiers, surfactants and emulsifiers, and cationic resins.

Other variations and modifications may be made in the compounds, compositions, and methods described herein without departing from the essential features and concepts of the present invention. The forms of the invention described herein are exemplary only and are not intended as limitations on the scope of the invention as defined in the appended claims.

That which is claimed is:

1. In a process for permanent waving of hair by a reaction in which cystine bridges are reduced to cysteine, the hair reshaped, and the reaction reversed, the improvement comprising reversing the reaction by applying to hair a composition comprising a vinyl functional silicone, hydrogen peroxide, and a carrier fluid selected from the group consisting of alcohols, hydrocarbons, halogenated hydrocarbons, volatiles silicones, water, and mixtures of water and alcohol, the vinyl functional silicone having a formula selected from the group consisting of:

$$Me_2ViSiO(MeViSiO)_xSiMe_2Vi$$

$$Me_2ViSiOSiMe_2Vi$$

-continued
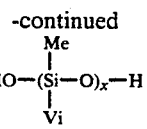

in which Me is the methyl radical —$CH_3$, Vi is the vinyl radical $CH_2=CH-$, and x is an integer having a value of from one to one thousand.

2. A process according to claim 1 in which the vinyl functional silicone is present in the form of a mechanical emulsion.

3. A process according to claim 1 in which the vinyl functional silicone is present in the form of an emulsion prepared by emulsion polymerization.

* * * * *